United States Patent [19]

Evans

[11] Patent Number: 5,208,345

[45] Date of Patent: May 4, 1993

[54] PROCESS FOR THE PRODUCTION OF (S)-VINYL AND ALLENYL GABA

[75] Inventor: Jonathan C. Evans, Midland, Mich.

[73] Assignee: Merrell Dow Pharmaceuticals Inc., Cincinnati, Ohio

[21] Appl. No.: 938,661

[22] Filed: Aug. 31, 1992

Related U.S. Application Data

[63] Continuation of Ser. No. 782,941, Oct. 25, 1991, abandoned, which is a continuation-in-part of Ser. No. 628,738, Dec. 17, 1990, abandoned.

[51] Int. Cl.$^5$ .................. C07F 7/02; C07D 207/12
[52] U.S. Cl. ......................... 548/406; 548/540
[58] Field of Search ................... 548/406, 540

[56] References Cited

U.S. PATENT DOCUMENTS

| | | | |
|---|---|---|---|
| 3,959,356 | 5/1976 | Metcalf et al. | 260/482 |
| 3,960,927 | 6/1976 | Metcalf et al. | 260/471 |
| 4,912,232 | 3/1990 | Mullins et al. | 548/539 |
| 4,939,126 | 7/1990 | Kurono et al. | 548/406 |

FOREIGN PATENT DOCUMENTS

| | | | |
|---|---|---|---|
| 0094886 | 5/1983 | European Pat. Off. | 548/539 |
| 0116257 | 12/1983 | European Pat. Off. | 548/539 |
| 0134481 | 7/1984 | European Pat. Off. | 548/539 |
| 0342613 | 5/1989 | European Pat. Off. | |

OTHER PUBLICATIONS

Chem Abstract vol. 109, 1988, p. 682; Abstract No. 190111b.
J. Amer. Chem. Soc., vol. 106, pp. 1877–1879 (1984).
*Stereoselection in the Reaction of Acid Halides and Vinylogous Urethanes,* Tetrahedron Letters, vol. 28, No. 45, pp. 5423–5426, 1987, Richard H. Schlessinger, et al.

*Primary Examiner*—Mary C. Lee
*Assistant Examiner*—Joseph K. McKane
*Attorney, Agent, or Firm*—J. Michael Dixon

[57] ABSTRACT

The present invention is directed to a new class of pyrrolidinone derivatives that are useful as chemical intermediates in the synthesis of S-allenyl and S-vinyl GABA, both of which are antiepileptic agents.

9 Claims, No Drawings

PROCESS FOR THE PRODUCTION OF (S)-VINYL AND ALLENYL GABA

CROSS-REFERENCE TO RELATED APPLICATION

This is a continuation, of application Ser. No. 782,941, filed Oct. 25, 1991, which is a continuation in part of application Ser. No. 628,738, filed Dec. 17, 1990, both now abandoned.

The present invention is directed to a stereospecific synthesis of (S)-vinyl-GABA, (S)-allenyl-GABA, (S)-5-allenylpyrrolidinone, and (S)-5-vinyl-pyrrolidinone. Another aspect is directed to a class of 1,5-disubstituted-pyrrolidinone intermediates as well as a new class of chiral lactic acid derivatives.

BACKGROUND OF THE INVENTION

4-Amino-5-hexenoic acid is known in the art as an antiepileptic agent and is described in U.S. Pat. No. 3,960,927. It is also known as vinyl-GABA and is currently available from Merrell Dow Pharmaceuticals, Inc. U.S. Pat. No. 4,621,145 (hereby incorporated by reference) describes one method for synthesizing this compound. The last step in the reaction sequence is depicted below:

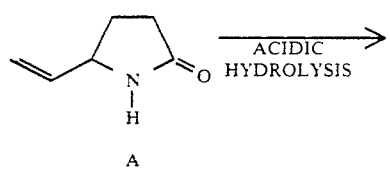

A

HO$_2$CCH$_2$CH$_2$CHCH=CH$_2$
|
NH$_2$

B

In this reaction 5-vinyl-2-pyrrolidinone (structure A) is subjected to an acidic hydrolysis thereby producing the desired compound, 4-amino-5-hexenoic acid (structure B). This acidic hydrolysis is carried out using techniques known in the art. Typically, the 5-vinyl-2-pyrrolidinone is contacted with a strong acid such as hydrochloric acid or trifluoroacetic acid at a temperature above 60° C. in an aqueous solvent system.

Co-pending U.S. patent application Ser. No. 432,707, filed Nov. 7, 1989 (which is hereby incorporated by reference) discloses that vinyl-GABA can be produced by subjecting 5-vinyl-2-pyrrolidinone to a basic hydrolysis as well. This hydrolysis is typically carried out by contacting the 5-vinyl-2-pyrrolidinone with a molar excess of potassium hydroxide. Typically from about 1.1 to about 1.5 equivalents are utilized. The basic hydrolysis is carried out at a temperature ranging from about 60° C. to 140° C. The reaction is typically carried out for a period of time ranging from about 0.5 hours to about 24 hours.

4-Amino-hepta-5,6-dienoic acid is also known in the art as an anti-epileptic agent and is described in U.S. Pat. No. 4,454,156. This compound is also known as allenic-GABA and is under development by Merrell Dow Pharmaceuticals, Inc. Castelhano et al. discloses that allenic-GABA (Structure E) can be produced by a hydrolysis similiar to that discussed above utilizing of 5-allenyl-2-pyrrolidinone (Structure D) as the starting material, *J. Am. Chem. Soc.* Vol. 106, pages 1877–1879 (1984). This reaction may be depicted as:

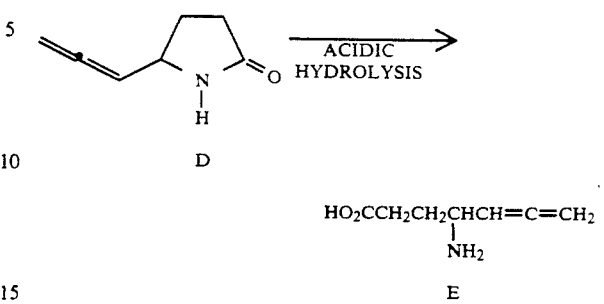

HO$_2$CCH$_2$CH$_2$CHCH=C=CH$_2$
|
NH$_2$

E

U.S. Pat. Nos. 4,621,145 and 4,454,156 disclose that the S-enantiomer of 4-amino-5-hexenoic acid and 4-amino-hepta-5,6-dienoic acid are the preferred isomers.

Recent efforts have focused on developing a commercially viable method for synthesizing the S-enantiomer of these compounds. The following synthetic procedure was developed as depicted by Reaction Scheme I:

REACTION SCHEME I

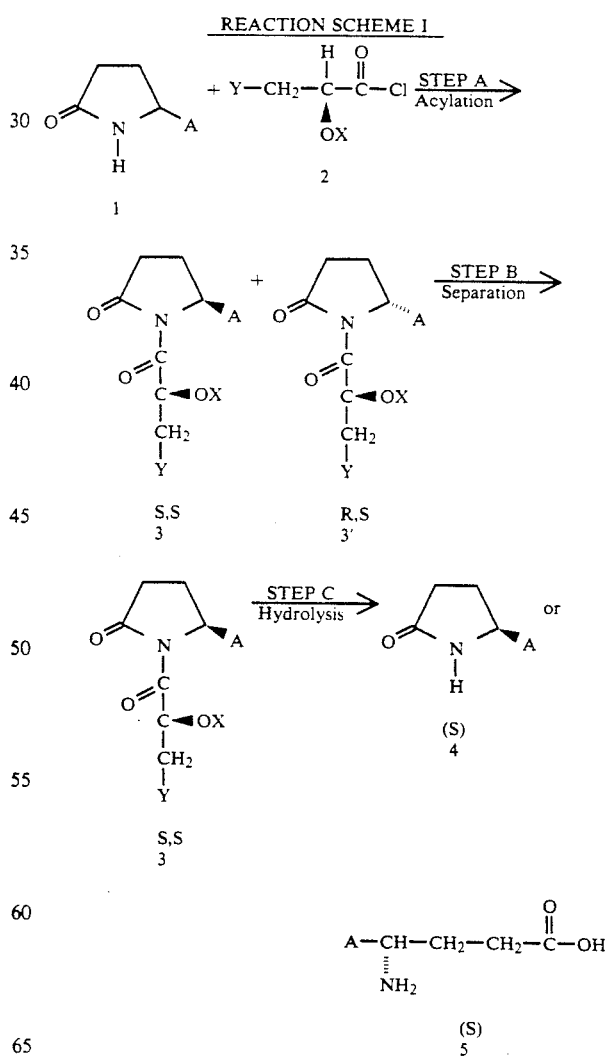

In Step A, a racemic pyrrolidinone derivative as described by structure 1 in which A is represented by —CH=C=CH₂ or —CH=CH₂, is acylated with a chiral auxiliary as described by structure 2 in which X and Y are simultaneously represented by the following substituents:

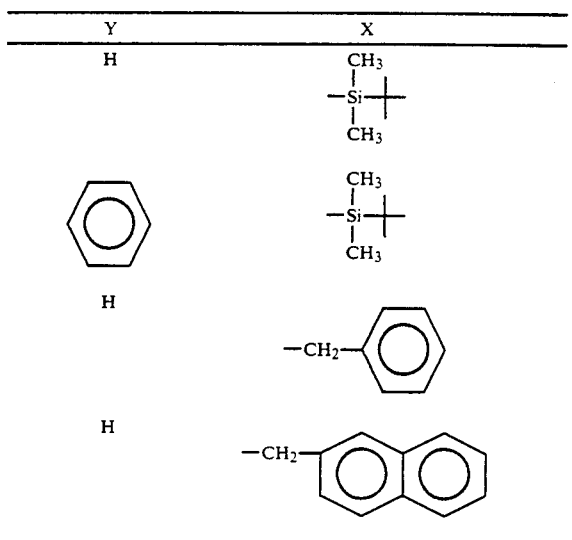

This acylation reaction produces the disastereomers described by structure 3 and 3' in which A, X, and Y are as defined above. In Step B the disastereomers are separated and the desired S,S isomer depicted by structure 3 is recovered. In Step C, this disastereomer is subjected to a hydrolysis reaction. Depending on the manner in which the hydrolysis is carried out, this reaction produces either the S-pyrroldinone derivative described by structure 4 or the (S)-amino acid derivative described by structure 5 in which A is as defined above.

The acylation reaction of Step A can be carried out using techniques known in the art. Typically the pyrrolidinone derivative of structure 1 is contacted with an approximately equivalent amount of a base such as sodium hydride, butyllithium, lithium diisopropylamine, potassium t-butoxide and potassium carbonate for a period of time ranging from 15 minuites to 3 hours. The reactants are typically contacted at a depressed temperature in the range of −40° C. to 25° C. in an aprotic solvent such as toluene, tetrahydrofuran, toluene/mineral oil, etc. The reaction medium is then warmed to approximately room temperature and an equivalent amount of the chiral auxiliary of structure 2 is added to the reaction. The reactants are typically stirred together for a period of time ranging from 1 minute to 3 hours. The reaction is then quenched by the addition of water and the diastereomers of structure 3 and 3' are recovered by extraction.

In Step B, the diastereomers are separated by techniques known in the art. One suitable method is flash chromatography on silica gel. Suitable eluants include hexane/ethyl acetate, t-butylmethyl ether/hexane and toluene. Another suitable separation method is recrystallization. Suitable solvent systems include polar solvents such as hexane/ethyl acetate or tetrahydrofuran.

In Step C, the (S,S)-diastereomer produced above is subjected to a hydrolysis reaction. Depending upon the manner in which the reaction is carried out, the product will either be the (S)-pyrrolidinone derivative of structure 4 or the (S)-amino acid derivative of structure 5. The pyrrolidinone derivative of Structure 4 can be produced by subjecting the diastereomer to a basic hydrolysis with a weak base such as $K_2CO_3$. This hydrolysis is typically carried out in methanol at a temperature range of from 25° C. to 65° C. for a period of time ranging from 1 to 4 hours. The amino acid derivative can be produced by subjecting the diastereomer to a hydrolysis with a stronger base such as potassium hydroxide in a solvent such as water. This hydrolysis is typically carried out at a temperature ranging from 50° C. to 140° C. for a period of time ranging from 1 to 24 hours. Alternatively, the amino acid derivative of structure 5 can be produced via an acidic hydrolysis in which hydrochloric acid is used.

An alternative method of producing either the (S)-pyrrolidinone of structure 4 or the (S)-amino acid of structure 5 is depicted below in Reaction Scheme II:

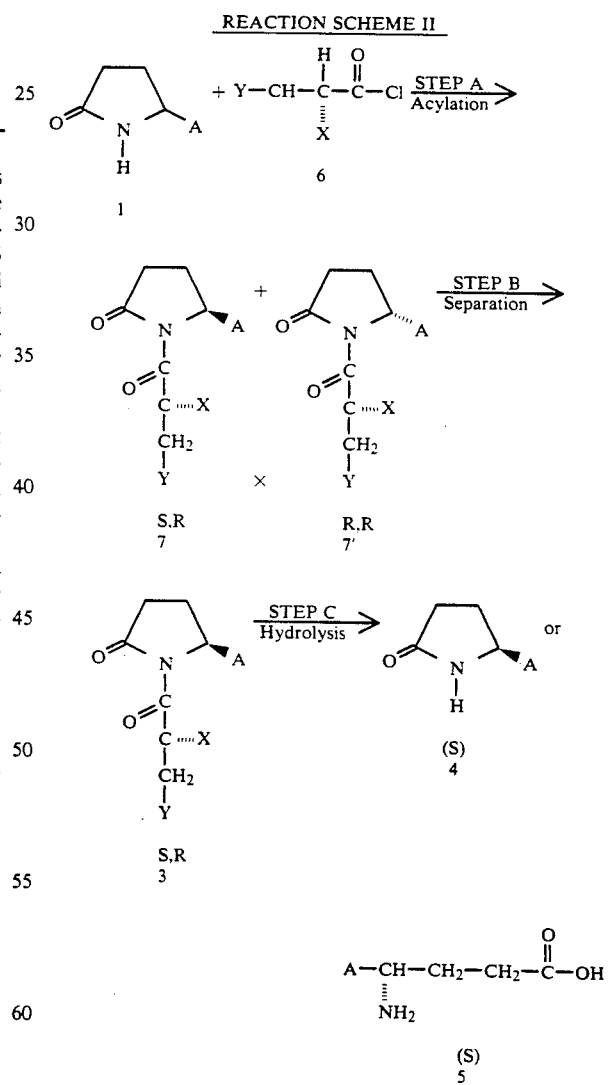

The initial step is to carry out an acylation reaction between the pyrrolidinone of structure 1 in which A is as defined above and the chiral auxiliary of structure 6 in which X and Y are simultaneously represented by

| Y | X |
|---|---|
| H | 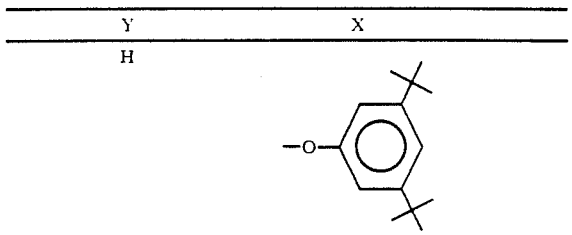 |
| H | |
| H | 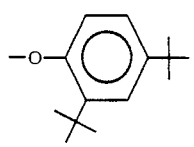 |
| H | 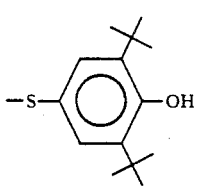 |

This acylation produces the diastereomers of structure 7 and 7'. This acylation can be carried out in the same manner discussed above for Step A of Reaction Scheme I. In Step B these diastereomers are separated and the (S,R)-diastereomer (7') is recovered for further processing. This separation can be carried out in the same manner as the separation of Step B in Reaction Scheme I. In Step C the diastereomer of structure 7 is subjected to a hydrolysis reaction thereby producing the (S)-pyrrolidinone derivative of structure 4 or the amino acid derivative of structure 5. This hydrolysis can be carried out in the same manner as above.

Methods for producing the chiral auxiliaries of structures 2 and 6 are known in the art. Specific methods are disclosed in Examples 1–7. Methods for producing the pyrrolidinones of structure 1 are known in the art.

The following examples are being presented in order to further illustrate the invention. They should not be construed as limiting the invention in any manner.

EXAMPLE 1

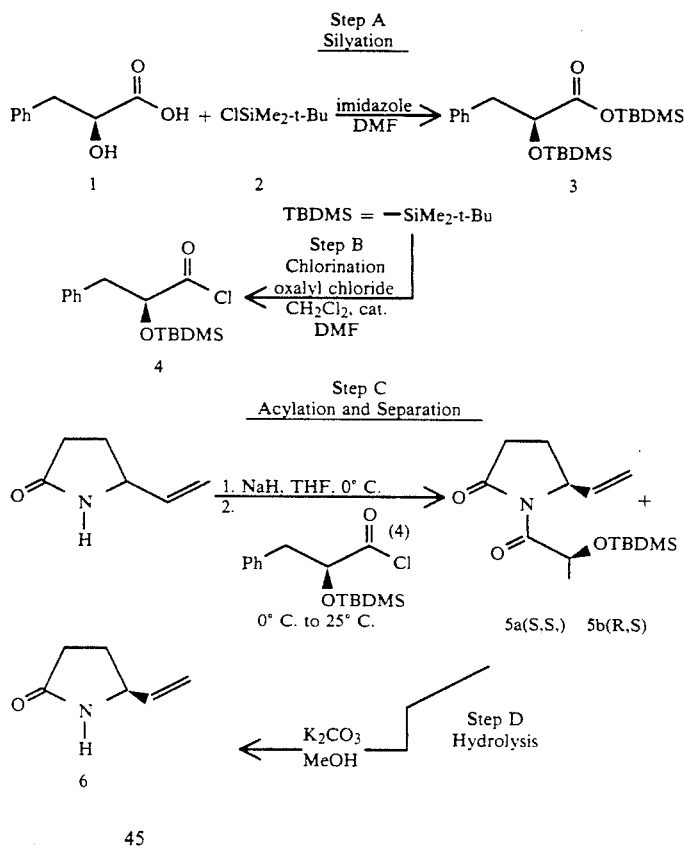

STEP A SILYATION (1,1-Dimethylethyl)dimethylsilyl (2S)-1((1,1-Dimethylethyl)dimethylsilyloxy)-3-phenylpropanoate To a solution of 10.04 g (60 mmol) of (2S)-3-phenyllacetic acid and 18.10 g (270 mmol) of imidazole in N,N-dimethylformamide (200 mL) was added 19.95 g (130 mmol) of t-butyldimethylchlorosilane at 25° C. The reaction mixture was stirred at room temperature for 18 hours under an argon atmosphere. To the reaction mixture was then added hexane (400 mL). The bi-phasic solution was stirred for 15 minutes prior to the addition of water (300 mL). The solution was stirred for 1 minute before the phases were separated. The organic phase was dried over magnesium sulfate. Concentration and vacuum distillation afforded 22.2 g (93%) of (1,1-dimethylethyl)dimethylsilyl (2S)-2-((1,1-dimethylethyl)-dimethylsilyloxy)-3-phenylpropanoate (3) as a clear liquid: bp 123°–125° C. (0.5 mm Hg); $^1$H NMR (CDCl$_3$) δ0.206 (s,3 H)), −0.0741 (s,3 H), 0.253 (s, 3 H), 0.273 (s, 3 H), 0.812 (s, 9 H), 0.942 (s, 9 H), 2.85–2.92 (m, 1 H), 3.05–3.11 (m, 1 H), 4.27–4.31 (m, 1 H), 7.21–7.31 (m, 5

H); $^{13}$C NMR (CDCl$_3$) δ173.2, 137.6, 129.8, 128.3, 126.5, 74.5, 41.7, 25.7, 25.6, 18.2, 17.7, −4.89, −5.19, −5.73.

STEP B CHLORINATION (2S)-2-((1,1-Dimethylethyl)dimethylsilyloxy)-3-phenyl-propanoyl chloride (4)

To a solution of 21.0 g (53 mmol) of (1,1-dimethylethyl)-dimethylsilyl (2S)-2-((1,1-dimethylethyl)dimethylsilyloxy)-3-phenylpropanoate (3) and five drops of N,N-dimethylformamide in methylene chloride at 0° C. was added 29.3 mL (59 mmol) of a 2.0M solution of oxalyl chloride in methylene chloride over a 30 min period. The cooling bath was removed and the reaction mixture was allowed to stir at room temperature for 18 hours. The solvent and excess oxalyl chloride were removed by rotary evaporation resulting in a yellow liquid. Purification by vacuum distillation afforded 12.7 g (80%) of (2S)-2-((1,1-dimethylethyl)-dimethylsilyloxy)-3-phenyl-propanoyl chloride (4) as a clear liquid: bp 88°-90° C. (0.2 mm Hg); $^1$H NMR (CDCl$_3$) δ−0.215 (s, 3 H), −0.0339 (s, 3 H), 0.840 (s, 9 H), 2.94–3.01 (m, 1 H), 3.23–3.29 (m, 1 H), 4.52–4.56 (m, 1 H), 7.25–7.35 (m, 5 H); $^{13}$C NMR (CDCl$_3$) δ175.7, 135.9, 129.8, 128.4, 127.1, 81.1, 40.8, 25.5, 18.0, −5.40, −5.76.

STEP C ACYLATION AND SEPARATION

N-Acylation of 5-Vinylpyrrolidin-2-one with (2S)-2-((1,1-dimethylethyl)dimethylsilyloxy)-3-phenyl-propanoyl chloride (4)

To 60% sodium hydride (336 mg. 10 mmol, in mineral oil) in tetrahydrofuran (20 mL) at 0° C. was added dropwise a solution of 5-vinylpyrrolidin-2-one (1.0 g, 9.0 mmol) in tetrahydrofuran (10 mL) over a 5 min period. The cooling bath was removed and the solution was allowed to warm to 25° C. to ensure complete anion generation. To the anion at 25° C. was added dropwise a solution of (2S)-2-((1,1-dimethylethyl)dimethyl-silyloxy)-3-phenylpropanoyl chloride (4, 2.98 g, 10 mmol) in tetrahydrofuran (10 mL) over a 5 min period. TLC indicated that the reaction was complete upon addition of the acid chloride (silica gel plates; hexane and ethyl acetate, 9:1). The solvent was removed by rotary evaporation affording a thick slug. The slug was dissolved in methylene chloride (75 mL) and washed with water (1×50 mL), a saturated aqueous sodium bicarbonate solution (1×50 mL) and dried (MgSO$_4$).

Concentration and purification by flash chromatography on silica gel (EM 60, 0.040–0.063 partical size, 230–400 Mesh, column size: 4.5 cm diameter×15 cm length) using hexane and ethyl acetate (19:1) afforded 1.54 g (46%) of (5S)-N-((2S)-2-((1,1-dimethylethyl)-dimethylsilyloxy)-3-phenylpropanoyl)-5-ethenylpyr-rolidin-2-one (5a) as a white crystalline material: mp 92°–93.5° C.; $^1$H NMR (CDCl$_3$) δ−0.316 (s,3 H), −0.217 (s,3 H), 0.703 (s, 9 H), 1.94 (t, J=9.6 Hz, 1 H), 2.29 (p, J=11.7 Hz, 1 H), 2.50–2.75 (m, 3 H), 3.11 (d, J=12.8 Hz, 1 H), 4.97–5.13 (m, 1 H), 5.12–5.18 (m, 2 H), 5.45 (d, J=9.8 Hz, 1 H), 5.75–5.86 (m, 1 H); $^{13}$C NMR (CDCl$_3$) δ175.1, 174.1, 137.9, 135.4, 130.0, 128.0, 126.4, 115.8, 74.2, 58.1, 41.2, 31.7, 25.5, 24.3, 18.1, −5.50, −5.76.

STEP D HYDROLYSIS (5S)-5-Ethenylpyrrolidin-2-one (6) From (5S)-N-((2S)-2-((1,1-dimethylethyl)dimethylsilyloxy)-3-phenylpropanoyl)-5-ethenylpyrrolidin-2-one (5a)

To a solution of 500 mg (1.0 mmol) of (5S)-N-((2S)-2-((1,1-dimethylethyl)dimethylsilyloxy)-3-phenyl-propanoyl)-5-ethenylpyrrolidin-2-one (5a) in methanol (20 mL) and water (5 mL) was added 152 mg (1.1 mmol) of potassium carbonate. The resulting reaction mixture was stirred at 25° C. for 1 hour before a sample was removed for TLC analysis. TLC was carried out on silica gel plates and eluted with hexane and ethyl acetate (2:1). An additional 20 mL of water was added and the solution was extracted with methylene chloride (2×15 mL). The aqueous layer was acidified to pH ~4 with dilute hydrochloric acid (1.0M) and extracted with methylene chloride (2×20 mL). The combined organic phases were dried over magnesium sulfate. Concentration and purification by flash chromatography on silica gel (EM 60, 0.040–0.063 partical size, 230–400 Mesh, column size: 3.5 cm diameter×12 cm length) using hexane and ethyl acetate (9:1) afforded (67%) of (5S)-5-ethenyl-2-pyrrolidinone (6) as a clear thick oil: $^1$H NMR (CDCl$_3$) δ1.77–1.88 (m, 1 H), 2.22–2.42 (m, 2 H), 4.13–4.19 (m, 1 H), 5.11 (d, J=10.0 Hz, 1 H), 5.22 (d, J=17.0 Hz, 1 H), 5.75–5.86 (m, 1 H), 7.16–7.32 (b, NH, 1 H); $^{13}$C NMR (CDCl$_3$) δ178.5, 138.6, 115.3, 56.6, 29.8, 27.8.

EXAMPLE 2

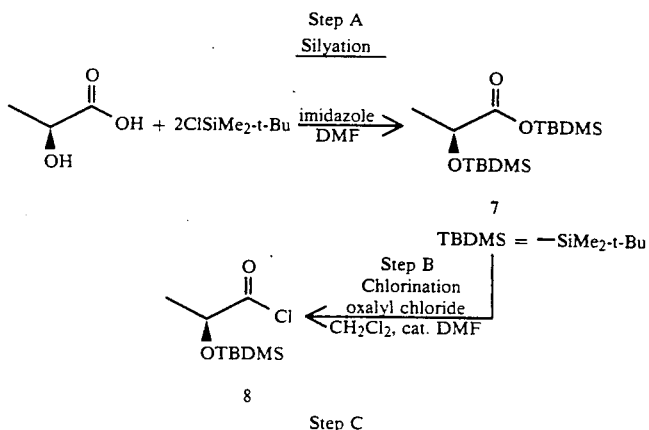

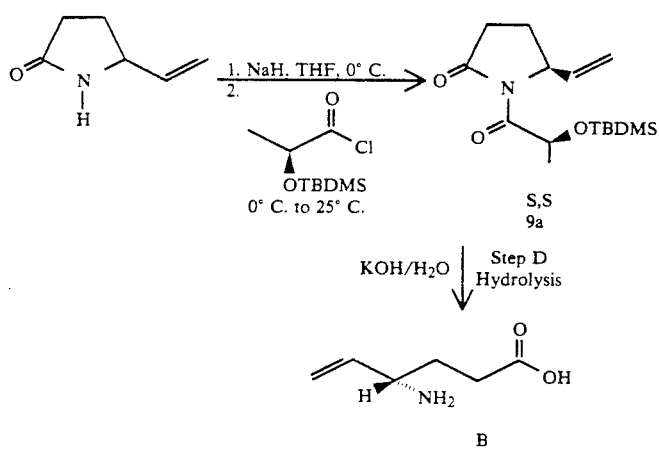

STEP A SILYATION (1,1-Dimethylethyl)dimethylsilyl (2S)-2-((1,1-dimethylethyl)dimethylsilyloxy)propanoate (7)

To a solution of 25.0 g (0.28 mol) of(2S)-lactic acid and 85.8 g (1.26 mol) of imidazole in N,N-dimethylformamide (400 mL) was added 92.0 g (0.62 mol) of t-butyldimethylchlorosilane at 25° C. The reaction mixture was stirred at room temperature for 18 hours under an argon atmosphere. To the reaction mixture was then added hexane (400 mL). The biphasic solution was stirred for 15 minutes prior to the addition of water (400 mL). The solution was stirred for 1 minute before the phases were separated. The organic phase was dried over magnesium sulfate. Concentration and vacuum distillation afforded 82.1 g (92%) of ((1,1-dimethylethyl)dimethylsilyl (2S)-2-(1,1-dimethylethyl)dimethylsilyloxy)propanoate (7) as a clear liquid: bp 83°-85° C. (0.02 mm Hg); $^1$H NMR (CDCl$_3$) $\delta$0.00836 (s, 3 H), 0.0608 (s, 3 H), 0.0962 (s, 6 H), 0.859 (s, 9 H), 0.934 (s, 9 H), 1.39 (d, J=6.7 Hz, 3 H), 4.25 (q, J=6.7 Hz, 1 H); $^{13}$C NMR (CDCl$_3$) $\delta$174.2, 69.1, 25.8, 25.6, 21.3, 18.3, 17.7, −4.83, −5.32.

STEP B CHLORINATION (2S)-2-((1,1-Dimethylethyl)dimethylsilyloxy)propanoyl chloride (8)

To a solution of 41.0 g (0.13 mol) of 2-(1,1-dimethylethyl)dimethylsilyl (2S)-2-((1,1-dimethylethyl)dimethylsilyloxy)propanoate (7) and five drops of N,N-dimethylformamide in methylene chloride at 0° C. was added 70.8 mL (0.14 mol) of a 2.0M solution of oxalyl chloride in methylene chloride over a 30 minute period. The cooling bath was removed and the reaction mixture was allowed to stir at room temperature for 18 hours. The solvent and excess oxalyl chloride were removed by rotary evaporation resulting in a yellow liquid. Purification by vacuum distillation afforded 25.6 g (88%) of (2S)-2-((1,1 -dimethylethyl)dimethylsilyloxy)propanoyl chloride (8) as a clear liquid: bp 42°-45° C. (1.5 mm Hg); $^1$H NMR (CDCl$_3$) $\delta$0.0920 (s, 3 H), 0.118 (s, 3 H), 0.909 (s, 9 H), 1.50 (d, J=6.7 Hz, 3 H), 4.49 (q, J=6.7 Hz, 1 H); $^{13}$C NMR (CDCl$_3$) $\delta$176.6, 76.0, 25.7, 25.6, 25.3, 20.9, 18.1, −1.57, −5.04, −5.28.

STEP C ACYLATION AND SEPARATION

N-Acylation of 5-Vinylpyrrolidin-2-one with (2S)-2-((1,1-Dimethylethyl)dimethylsilyloxy)propanoyl chloride (8)

To 60% sodium hydride (336 mg, 10 mmol) in mineral oil) in tetrahydrofuran (20 mL) at 0° C. was added dropwise a solution of 5-vinylpyrrolidin-2-one (1.0 g, 9.0 mmol) in tetrahydrofuran (10 mL) over a 5 minute period. The cooling bath was removed and the solution was allowed to warm to 25° C. to ensure complete anion generation. To the anion at 25° C. was added dropwise a solution of. (2S)-2-((1,1-dimethylethyl)dimethylsilyloxy)propanoyl chloride (2.23 g, 10 mmol) in tetrahydrofuran (10 mL) over a 5 minute period. TLC indicated that the reaction was complete upon addition of the acid chloride (silica gel plates; hexane and ethyl acetate, 9:1). The solvent was removed by rotary evaporation affording a thick slug. The slug was dissolved in methylene chloride (75 mL) and washed with water (1×50 mL) and dried (MgSO$_4$). Concentration and purification by flash chromatography on silica gel (EM 60, 0.040-0.063 partical size, 230-400 Mesh, column size: 4.5 cm diameter×15 cm length) using hexane and ethyl acetate (19:1) afforded 1.40 g (47%) of (5S)-N-((2S)-2-((1,1-dimethylethyl)dimethylsilyloxy)-propanoyl)-5-ethenylpyrrolidin-2-one (9a) as clear liquid: $^1$H NMR (CDCl$_3$) $\delta$0.0300 (s,3 H), 0.0656 (s, 3 H), 0.877 (s, 9 H), 1.37 (d, J=6.5 Hz, 3 H), 1.82-1.88 (m, 1 H) 2.21 (p, J=10.7 Hz, 1 H), 2.34–2.47 (m, 1 H), 2.60 (p, J=9.8 Hz, 1 H), 4.88 (br, 1 H), 5.05-5.11 (m, 2 H), 5.36-5.38 (m, 1 H), 5.70-5.79 (m, 1 H); $^{13}$C NMR (CDCl$_3$) $\delta$174.86, 174.77, 135.5, 115.4, 66.8, 57.9, 31.6, 25.5, 24.4, 21.1, 18.1, −4.87, −5.16.

STEP D HYDROLYSIS (4S)-Amino-5-hexenoic Acid (B) from (5S)-N-((2S)-2-((1,1-Dimethylethyl)dimethylsilyloxy)-propanoyl)-5-ethenylpyrrolidin-2-one (9a)

To a solution of diastereomer 9a (2.0 g, 6.7 mmol) in water (2 mL) is added 87% potassium hydroxide (1.2 g, 21.6 mmol). The resulting solution is refluxed 1 hour. The solution is allowed to cool to room temperature and resulting in two phases. The top phase is bis((1,1-dimethylethyl)dimethylsilyl)oxide. The phases are separated and the aqueous phase is extracted with methylene chloride (3×5 mL). The aqueous phase is diluted with isopropyl alcohol (15 mL) and ethanol (15 mL) to increase the solubility of the newly formed lactic acid. the solution is acidified to pH 5.5 with concentrated hydrochloric acid and extracted with diethyl ether (3×25 mL). Concentration of the extracts affords (4S)-amino-5-hexenoic acid (B).
EXAMPLE 3
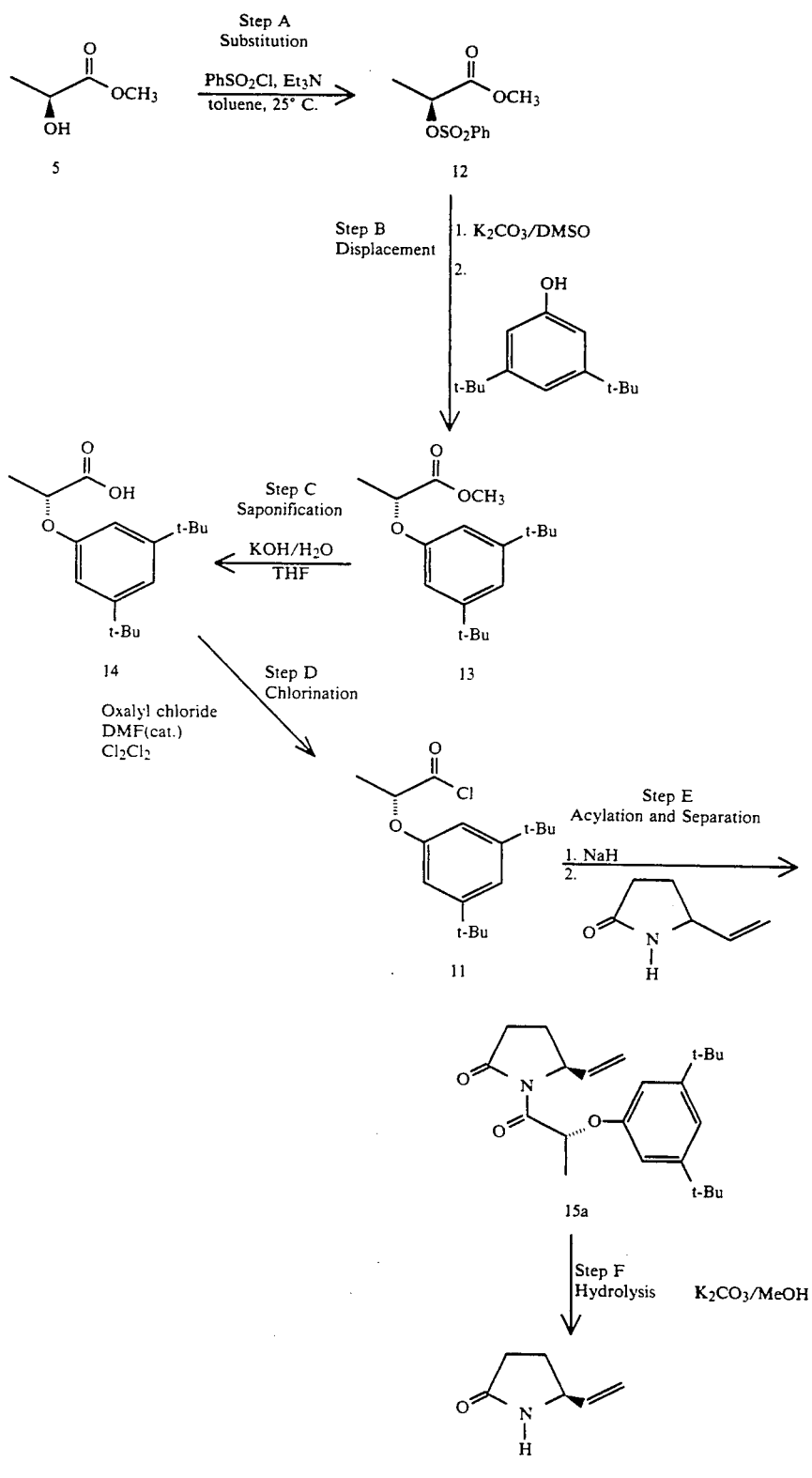

STEP A SUBSTITUTION

Methyl (2S)-2-(Phenylsulfonyl)oxypropanate (12)

To a solution of 200g (1.92 mol) of methyl (2S)-lactate (5) and 295 g (2.11 mol) of triethylamine in toluene (1 L) at 0° C. was added 270 mL, 2.11 mol) of benzenesulfonyl chloride dropwise over a 2 hour period under a nitrogen atmosphere. The cooling bath was removed and the reaction mixture was allowed to warm to room temperature and stir there overnight. The reaction was worked-up by washing with water (3×1 L) and dried (MgSO$_4$). Filtration, concentration and purification by vacuum distillation afforded 440 g (94%) of methyl (2S)-2-(phenylsulfonyl)oxypropanate (12) as a pale yellow liquid: bp 140°–142° C. (0.1 mm Hg); $^1$H NMR (CDCl$_3$) δ1.51–1.56 (d, 3 H), 3.66 (s, 3 H), 4.95–5.01 (q, 1 H), 7.54–7.59 (m, 2 H), 7.65–7.70 (m, 1 H), 7.93–7.95 (d, 2 H); $^{13}$C NMR (CDCl$_3$) δ169.3, 133.9, 129.1, 127.7, 112.3, 74.2, 52.5, 18.3; IR (neat) 2958 (w), 1762 (s), 1586 (m), 1451 (s), 1190 (vs), 1084 (s), 926 (m), 753 (m) cm$^{-1}$.

STEP B DISPLACEMENT

Methyl (2R)-2-(3,5-di-t-butylphenyloxy)propanate (13)

To a solution 8.87 g (43 mmol) of 3,5-di-t-buthylphenol in dimethyl sulfoxide (150 mL) was 26.9 mL (43 mmol) of a 1.6M n-butyllithium/hexane solution dropwise over a 15 min period under a nitrogen atmosphere. The solution was allowed to stir at room temperature for an additional 15 min resulting in the precipitation of the lithium salt of 3,5-di-t-buthylphenol. A solution of 10.0 g (40 mmol) of methyl (2S)-2-(phenylsulfonyl)oxypropanate (12) in dimethyl sulfoxide (50 mL) was added dropwise to the suspension over a 10 min period. The reaction mixture was stirred overnight at room temperature. To the reaction solution was added water (300 mL) and the product was extracted with perchloroethylene (3×200 mL). The combined organic extracts were washed with water (1×200 mL), an aqueous saturated sodium chloride solution (1×200 mL) and dried (MgSO$_4$). Filtration, concentration and purification by flash chromatography on silica gel (EM silica gel 60, 0.040–0.063 partical size, 230–400 Mesh, column size: 7 cm diameter×18 cm length) using hexane and ethyl acetate (19:1) afforded 11.75 g (89%) of methyl (2R)-2-(3,5-di-t-butylphenyloxy)propanate (13) as a thick oil: $^1$H NMR (CDCl$_3$) δ 1.29 (s, 18 H), 1.61–1.63 (d, 3 H), 3.76 (s, 3 H), 4.75–4.82 (q, 1 H), 6.73 (s, 2 H), 7.04 (s, 1 H); $^{13}$C NMR (CDCl$_3$) δ173.1, 157.2, 152.3, 115.8, 114.7, 109.7, 109.5, 72.7, 52.1, 34.9, 31.4, 18.6.

STEP C DEPROTECTION (2R)-2-(3,5-Di-t-butylphenyloxy)propanoic Acid (14)

To a solution of 2.0 g (36 mmol) of potassium hydroxide in water (100 mL) and tetrahydrofuran (100 mL) was added 11.48 g (36 mmol) of methyl (2R)-2-(3,5-di-t-butylphenyloxy)propanate (13). The reaction mixture was allowed to stir overnight at room temperature. The reaction mixture was acidified to pH 2 with concentrated hydrochloric acid and the resulting solution was extracted with diethyl ether (3×200 mL). The combined extracts were washed with an aqueous saturated sodium chloride solution (1×300 mL) and dried (MgSO$_4$). Filtration and concentration resulted in a yellowish sludge. The crude product was purified by precipitation from hexane at −78° C. to afford 8.2 g (75%) of (2R)-2-(3,5-di-t-butylphenyloxy)propanoic acid (14) as an off-white crystalline material: $^1$H NMR (CDCl$_3$) δ1.29 (s, 18 H), 1.64–1.66 (d, 3 H), 4.56–4.82 (q, 1 H), 6.75 (s, 2 H), 7.06 (s, 1 H); $^{13}$C NMR (CDCl$_3$) δ177.7, 156.8, 152.5, 116.2, 109.7, 72.3, 35.0, 31.4, 18.4.

STEP D CHLORINATION (2R)-2-(3,5-Di-t-butylphenyloxy)propanoyl chloride (11)

To a mixture of 3.0 g (9.8 mmol) of (2R)-2-(3,5-di-t-butylphenyloxy)propanonic acid (14) and 4 drops of N,N-dimethylformamide in methylene chloride (50 mL) at 0° C. under a nitrogen atmosphere was added 5.4 mL (10.8 mmol) of a 2M solution of oxalyl chloride in methylene chloride dropwise over a 20 min period. The reaction mixture was allowed to stir at room temperature overnight. The solvent and any excess oxalyl chloride was removed by rotary evaporation and dried (under vacuum) to afford 3.15 g (99%) of crude (2R)-2-(3,5-di-t-butylphenyloxy)propanoyl chloride (11) as yellowish liquid: $^1$H NMR (CDCl$_3$) δ1.30 (s, 18 H), 1.73–1.76 (d, 3 H), 4.92–4.98 (q, 1 H), 6.72 (s, 2 H), 7.10 (s, 1 H); $^{13}$C NMR (CDCl$_3$) δ175.0, 156.5, 152.7, 116.7, 109.7, 79.8, 35.0, 31.4, 18.1.

STEP E ACYLATION AND SEPARATION

N-Acylation of 5-Vinylpyrrolidin-2-one with (2R)-2-(3,5-Di-t-butylphenyloxy)propanoyl chloride (11)

To 60% sodium hydride (336 mg, 10 mmol) in toluene (20 mL) at 0° C. was added dropwise a solution of 5-vinylpyrrolidin-2-one (1.0 g, 9.0 mmol) in toluene (10 mL) over a 5 min period. The cooling bath was removed and the solution was allowed to warm to 25° C. to ensure complete generation of the anion. To the anion at 25° C. was added dropwise a solution of (2R)-2-(3,5-di-t-butylphenyloxy)propanoyl chloride (11, 3.20 g, 9.8 mmol) in toluene (10 mL) over a 5 min period. TLC indicated that the reaction was complete upon addition of the acid chloride (silica gel plates; hexane and ethyl acetate, 2:1). Water (60 mL) was added to the reaction mixture and the phases were separated. The aqueous phase was extracted with ethylene chloride (1×40 mL). The combined organic phases were washed with a saturated aqeous sodium bicarbonate solution (1×70 mL) and dried (MgSO$_4$). Concentration and purification by flash chromatography on silica gel (EM silica gel 60, 0.040–0.063 partical size, 230–400 Mesh, column size: 6.5 cm diameter×18 cm length) using hexane and ethyl acetate (19:1) afforded 1.65 g (46%) of (5S)-N-((2S)-2-(3,5-di-t-butylphenyloxy)propanoyl)-5-ethenylpyrrolidin-2-one (15a) as an oil: $^1$H NMR (CDCl$_3$) δ1.20 (s, 18 H), 1.60–1.62 (d, 3 H), 1.92–2.04 (m, 1 H), 2.21–2.32 (m, 1 H), 2.52–2.80 (m, 2 H), 4.9–4.96 (q, 1 H), 5.11–5.21 (m, 2 H), 5.77–5.88 (m, 1 H), 5.98–6.04 (q, 1 H), 6.71 (s, 2 H), 7.00 (s, 1 H); $^{13}$C NMR (CDCl$_3$) δ175.2, 172.7, 157.1, 152.1, 135.2, 115.9, 115.6, 109.6, 72.3, 58.0, 34.9, 31.6, 31.4, 24.4, 18.1; IR (neat) 2966 (vs), 1740 (vs), 1715 (vs), 1593 (s), 1380 (s), 1229 (vs), 706 (w) cm$^{-1}$.

STEP F HYDROLYSIS (5S)-5-Ethenyl-2-pyrrolidin-2-one (6) from (5S)-N-((2S)-2-(3,5-Di-t-butylphenyloxy)propanoyl-5-ethenylpyrrolidin-2-one (15a)

A solution of diastereomer 15a (1.5 g, 3.8 mmol), potassium carbonate (233 mg, 1.7 mmol), and methanol (20 mL) is stirred at room temperature for 1.5 hours. The solvent is removed by rotary evaporation to afford a thick yellow oil. This oil is dissolved in methylene chloride (10 mL) and filtered through a silica gel plug (20 g, EM-60, 70-230 mesh) to remove any salts. The plug is rinsed with hexane/ethyl acetate (4:1), discarding the initial eluent which contains the chiral auxiliary, to give (5S)-5-ethenylpyrrolidin-2-one (6).

length) using hexane and ethyl acetate (29:1) afforded 10.1 g (77%) of methyl (2R)-2-(2,4-di-t-butylphenyloxy)propanate (17) as a thick oil: $^1$H NMR (CDCl$_3$) δ1.29 (s, 9 H), 1.43 (s, 9 H), 1.60–1.65 (d, 3 H), 3.73 (s, 3 H), 4.75–4.82 (q, 1 H), 6.54–6.57 (d, 1 H), 7.08–7.12 (d, 1 H), 7.33 (s, 1 H); $^{13}$C NMR (CDCl$_3$) δ172.9, 153.7, 143.0, 137.2, 124.2, 123.1, 110.5, 71.7, 52.0, 5.0, 34.2, 31.5, 29.9, 18.6; IR (neat) 2962 (vs), 1764 (s), 1740 (s), 1497 (s), 1235

EXAMPLE 4

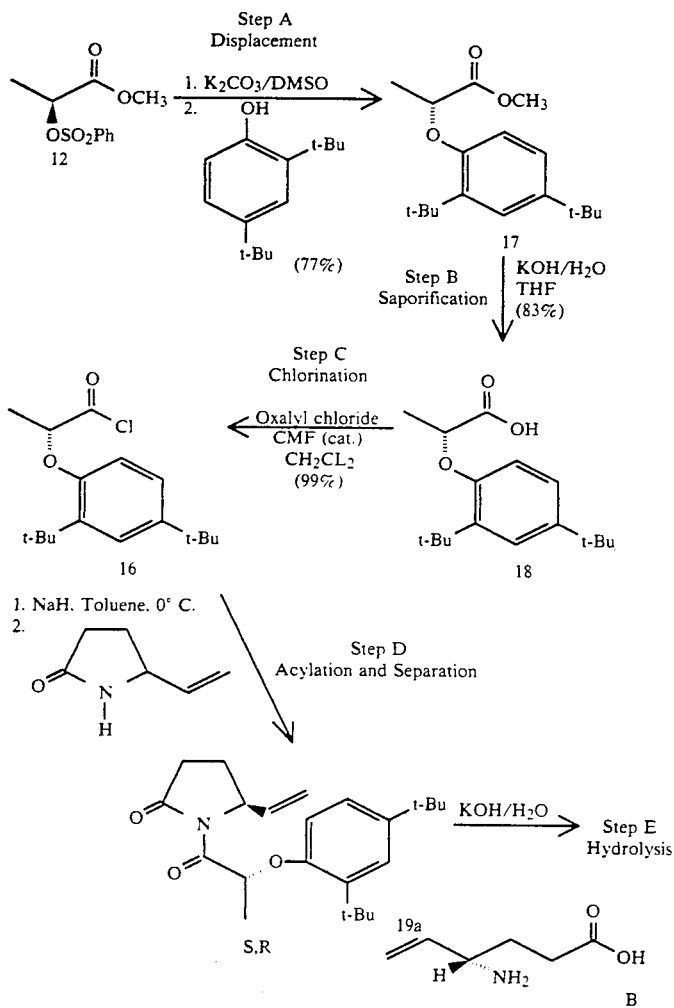

STEP A DISPLACEMENT

Methyl (2R)-2-(2,4-Di-t-butylphenyloxy)propanate (17)

Potassium carbonate (5.66 g, 41 mmol) and 2,4-di-t-butylphenol (8.87 g, 43 mmol) were dissolved in dimethyl sulfoxide (175 mL) at 25° C. and allowed to stir overnight under a nitrogen atmosphere to ensure complete anion formation. A solution of 10.0 g (41 mmol) of methyl (2S)-2-(phenylsulfonyl)oxypropanate (12) in dimethyl sulfoxide (50 mL) was added to the anion at 25° C. and the reaction mixture was allowed to stir overnight. The reaction was quenched with water (200 mL) and the phases were separated. The aqueous phase was extracted with perchloroethylene (3×200 mL). The combined organic extracts were washed with water (3×300 mL), a saturated aqueous sodium chloride solution (1×300 mL) and dried (MgSO$_4$). Concentration and purification by flash chromatography on silica gel (EM silica gel 60, 0.040–0.063 partical size, 230–400 Mesh, column size: 7 cm diameter×18 cm length) using hexane and ethyl acetate (29:1) afforded (vs) cm$^{-1}$.

STEP B DEPROTECTION (2R)-2-(2,4-Di-t-butylphenyloxy)propanoic Acid (18)

To a solution of 5.98 mg (11 mmol) of potassium hydroxide in water (75 mL) and tetrahydrofuran (75 mL) was added 3.34 mg (10 mmol) of methyl (2R)-2-(2,4-di-t-butylphenyloxy)propanate (17). The reaction mixture was allowed to stir overnight at room temperature. The reaction mixture was acidified to pH 2 with concentrated hydrochloric acid and the resulting solution was extracted with diethyl ether (3×200 mL). The combined extracts were washed with an aqueous saturated sodium chloride solution (1×300 mL) and dried (MgSO$_4$). Filtration and concentration afforded a thick crude oil. Purification by precipitation from hexane at −78° C. afforded 2.65 g (83%) of (2R)-2-(2,4-di-t-butylphenyloxy)propanoic acid (18) as a white crystalline material: ¹H NMR (CDCl₃) δ1.29 (s, 9 H), 1.42 (s, 9 H), 1.68-1.70 (d, 3 H), 4.77-4.85 9q, 1 H), 6.58-6.61 (d, 1 H), 7.11-7.15 (d, 1 H), 7.34 (s, 1 H); ¹³C NMR (CDCl₃) δ177.2, 153.5, 143.3, 137.3, 124.4, 123.3, 110.7, 71.4, 35.0, 34.3, 31.6, 30.0, 18.5.

STEP C CHLORINATION (2R)-2-(2,4-Di-t-butylphenyloxy)propanoyl chloride (16)

To a mixture of 675 m9 (2.2 mmol) of (2R)-2-(2,4-di-t-butylphenyloxy)propanoic acid (18) and 4 drops of N,N-dimethylformamide in methylene chloride (20 mL) at 0° C. under a nitrogen atmophere was added 1.21 mL (2.4 mmol) of a 2M solution of oxalyl chloride in methylene chloride dropwise over a 10 min period. The reaction mixture was allowed to stir at room temperature overnight. The solvent and any excess oxalyl chloride was removed by rotary evaporation and dried (under vacuum) to afford 715 mg (99%) of (2R)-2-(2,4-di-t-butylphenyloxy)propanoyl chloride (16) as a crude yellow liquid: ¹H NMR (CDCl₃) δ1.29 (s, 9 H), 1.42 (s, 9 H), 1.76-1.79 (d, 3 H), 4.94-5.00 (q, 1 H), 6.50-6.(d, 1 H), 7.12-7.16 (d, 1 H), 7.36 (s, 1 H); ¹³C NMR (CDCl₃) δ175.0, 152.8, 144.1, 137.4, 124.6, 123.4, 110.6, 78.6, 35.1, 34.3, 1.5, 30.0, 18.0.

STEP D ACYLATION AND SEPARATION

N-Acylation of 5-Vinylpyrrolidin-2-one with (2R)-2-(2,4-Di-t-butylphenyloxy)propanoyl chloride (16)

To 60% sodium hydride (74 mg, 2.2 mmol) in toluene (10 mL) at 0° C. was added dropwise a solution of 5-vinylpyrrolidin-2-one (222 mg, 2.0 mmol) in toluene (5 mL) over a 5 min period. The cooling bath was removed and the solution was allowed to warm to 25° C. to ensure complete generation of the anion. To the anion at 25° C. was added dropwise a solution of (2R)-2-(2,4-di-t-butylphenyloxy)propanoyl chloride (16, 716 mg, 2.2 mmol) in toluene (5 mL) over a 5 min period. TLC indicated that the reaction was complete upon addition of the acid chloride (silica gel plates; hexane and ethyl acetate, 4:1). Water (30 mL) was added to the reaction mixture and the phases were separated. The aqueous phase was extracted with methylene chloride (1×25 mL). The combined organic phases were washed with a saturated aqeous sodium bicarbonate solution (1×50 mL) and dried (MgSO₄). Concentration and purification by flash chromatography on silica gel (EM silica gel 60, 0.040-0.063 partical size, 230-400 Mesh, column size: 4.5 cm diameter×15 cm length) using hexane and ethyl acetate (19:1) afforded 360 mg (45%) of (5S)-N-((2R)-2-(2,4-di-t-butylphenyloxy)-propanoyl)-5-ethenylpyrrolidin-2-one (19a) as a thick oil: ¹H NMR (CDCl₃) δ1.28 (s, 9 H), 1.42 (s, 9 H), 1.77-1.80 (d, 3 H), 1.95-2.10 (m, 1 H), 2.23-2.33 (m, 1 H), 2.52-2.82 (m, 2 H), 4.91-4.97 (q, 1 H), 5.10-5.19 (m, 2 H), 5.80-5.90 (m, 1 H), 5.97-6.03 (m, 1 H), 6.49-6.53 (d, 1 H), 7.12-7.16 (d, 1 H), 7.35 (s, 1 H); ¹³C NMR (CDCl₃) δ175.4, 172.9, 157.3, 153.4, 143.1, 137.2, 135.6, 124.3, 123.2, 115.8, 71.6, 57.9, 35.2, 34.2, 31.9, 31.4, 29.9, 24.3, 18.2; IR (neat) 2965 (vs), 1741 (vs), 1715 (vs), 1590 (s), 1230 (vs), 710 (w) cm⁻¹.

STEP E HYDROLYSIS (4S)-Amino-5-hexenoic Acid (B) from (5S)-N-((2R)-2-(2,4-Di-t-butylphenyloxy)propanoyl)-5-ethenylpyrrolidin-2-one (19a)

A solution of (5S)-N-((2R)-2-(2,4-di-t-butylphenyloxy)-propanoyl)-5-ethenylpyrrolidin-2-one (19a, 1.0 g, 2.5 mmol) and 87% potassium hydroxide (317 mg, 5.7 mmol) in water (2 mL) is refluxed for 1.5 hours. The solution is allowed to cool to room temperature. Water is added (15 mL) and the solution is acidified to pH 7 with concentrated hydrochloric acid and extracted with diethyl ether (3×10 mL) to remove the chiral auxiliary. The aqueous solution is then acidified to pH 5.5 with concentrated hydrochloric acid and extracted with diethyl ether (3×15 mL). The second series of organic extracts are combined and dried (MgSO₄). Concentration by rotary evaporation affords (4S)-4-amino-5-hexenoic acid (B).

EXAMPLE 5

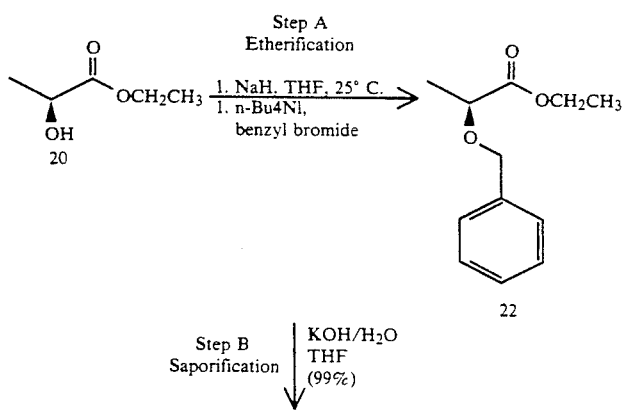

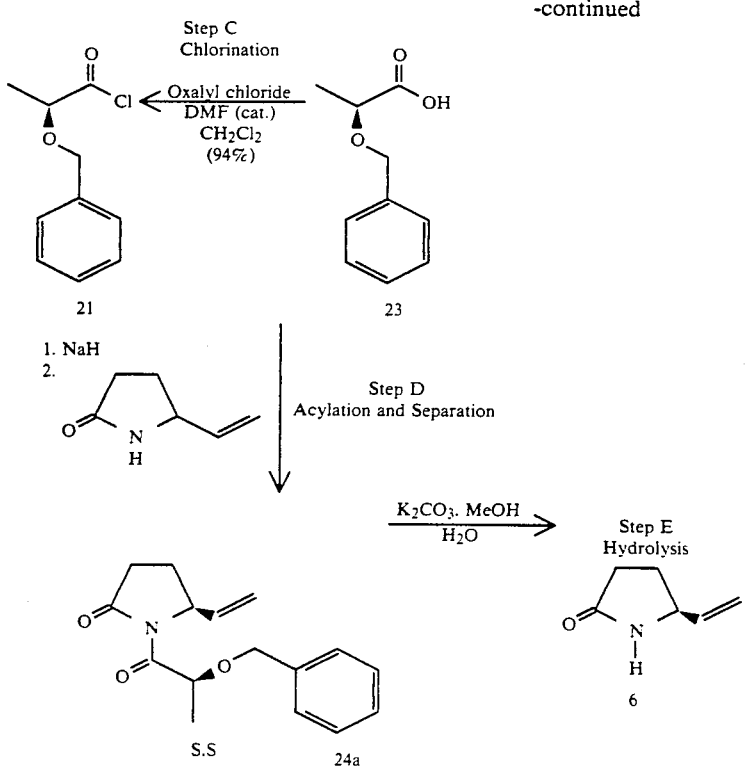

STEP A ETHERIFICATION

Ethyl (2S)-2-benzoylpropanate (22)

To a slurry of 3.13 g (93 mmol) of sodium hydride (60% in mineral oil) in tetrahydrofuran (150 mL) at 25° C. was added a solution of 10.0 g (85 mmol) of (S)-ethyl lactate (20) in tetrahydrofuran (50 mL) dropwise over a 30 min period under a nitrogen atmosphere. The resulting solution was then allowed to stir at 25° C. for an additional 30 min to ensure complete anion formation. To the anion was added 33.2 g (90 mmol) of tetra-n-butylammoniun iodide. A solution of 10.3 mL (93 mmol) of benzyl bromide in tetrahydrofuran (50 mL) was added dropwise to the reaction mixture over a 30 min period. The reaction was complete within 2 h at 25° C., during which time a solid precipitate formed. The reaction mixture was filtered through a coarse sintered glass funnel containing Celite. The solid was washed with diethyl ether (50 mL). The filtrate was washed with a saturated aqueous sodium chloride solution (3×300 mL) and dried (MgSO₄). Concentration and purification by flash chromatography on silica gel (EM 60, 0.040-0.063 partical size, 230-400 Mesh, column size: 7 cm diameter×20 cm length) using hexane and ethyl acetate (9:1) afforded 13.2 g (75%) of ethyl (2S)-2-benzoylpropanate (22) as a yellowish liquid: $^1$H (CDCl₃) δ1.26-1.31 (t, J=7.1 Hz, 3 H), 1.42-1.44 (d, J=6.8 Hz, 2 H), 4.01-4.12 (m, 1 H), 4.17-4.24 (q, J=7.0 Hz, 2 H), 4.42-4.46 (d, J=11.6 Hz, 1 H), 4.67-4.71 (d, J=11.6 Hz, 1 H), 7.28-7.38 (m, 5 H); $^{13}$C NMR (CDCl₃) δ173.0, 137.6, 128.3, 127.8, 127.7, 74.1, 71.9, 60.6, 18.5, 14.1; IR (neat) 2985 (s), 1746 (vs), 1455 (s), 1200 (s), 1144 (vs), 698 (vs) cm⁻¹.

STEP B DEPROTECTION

(2S)-2-Benzoylpropanonic Acid (23)

To a solution of 4.2 g (74 mmol) of potassium hydroxide in water (150 mL) and tetrahydrofuran (150 mL) was added 10.9 g (52 mmol) of ethyl (2S)-2-benzoylpropanate (22). The reaction mixture was allowed to stir overnight at room temperature. The reaction solution was acidified to pH 2 with concentrated hydrochloric acid and and extracted with diethyl ether (3×150 mL). The combined extracts were washed with an aqueous saturated sodium chloride solution (1×300 mL) and dried (MgSO₄). Filtration and concentration afforded 9.4 g (99%) of crude (2S)-2-benzoylpropanonic acid (23) as an oil: $^1$H NMR (CDCl₃) δ1.45-1.48 (d, J=6.9 Hz, 3 H), 4.05-4.12 (q, J=6.9 Hz, 1 H), 4.45-4.49 (d, J=11.6 Hz, 1 H), 4.69-4.73 (d, J=11.6 Hz, 1 H), 7.27-7.35 (m, 5 H), 9.14 (br, 1 H); $^{13}$C NMR (CDCl₃) δ177.8, 137.1, 128.3, 127.8, 73.4, 71.9, 18.2; IR (neat) 3855-2615 (br), 2989 (s), 1719 (vs), 1457 (s), 1115 (vs), 737 (w), 698 (s) cm⁻¹.

STEP C CHLORINATION

(2S)-2-Benzoylpropanoyl Chloride (21)

To a mixture of 9.0 g (50 mmol) of (2S)-2-benzoylpropanonic acid (23) and 5 drops of N,N-dimethylformamide in methylene chloride (200 mL) at 0° C. under a nitrogen atmosphere was added 27.5 mL (55 mmol) of a 2M solution of oxalyl chloride in methylene chloride dropwise over a 30 min period. The reaction mixture was allowed to stir at room temperature overnight. The solvent and any excess oxalyl chloride was removed by rotary evaporation and dried (under vacuum) to afford 10.5 g (98%) of (2S)-2-benzoylpropanoyl chloride (21 as a crude yellow liquid: $^1$H NMR (CDCl₃) δ1.51-1.53 (d, J=6.8 Hz, 3 H), 4.22-4.28 (q, J=6.8 Hz, 1 H), 4.41-4.44

(d, J=11.4 Hz, 1 H), 4.70-4.73 (d, J=11.4 Hz, 1 H), 7.33-7.35 (m, 5 H); IR (neat) 3067 (w), 3035 (s), 2992 (w), 2875 (w), 1831 (vs), 1781 (vs), 1454 (vs), 1154 (s), 735 (s), 699 (s) cm$^{-1}$.

STEP D ACYLATION AND SEPARATION

N-Acylation of 5-Vinylpyrrolidin-2-one with (2S)-2-Benzoylpropanoyl Chloride (21)

To 60% sodium hydride (336 mg, 10.0 mmol) in toluene (20 mL) at 0° C. was added dropwise a solution of 5-vinylpyrrolidin-2-one (1.0 mg, 9.0 mmol) in toluene (10 mL) over a 10 min period. The cooling bath was removed and the solution was allowed to warm to 25° C. to ensure complete generation of the anion. To the anion at 25° C. was added dropwise a solution of (2S)-2-benzoylpropanoyl chloride (21, 2.7 g, 12.6 mmol) in toluene (10 mL) over a 10 min period. TLC indicated that the reaction was complete upon addition of the acid chloride (silica gel plates; hexane and t-butyl methyl ether, 1:1). Water (50 mL) as added to the reaction mixture and the phases were separated. The aqueous phase was extracted with diethyl ether (2×40 mL). The combined organic phases were washed with a saturated aqeous sodium bicarbonate solution (1×100 mL) and dried (MgSO$_4$). Concentration and purification by flash chromatography on silica gel (EM 60, 0.040-0.063 partical size, 230-400 Mesh, column size: 6.5 cm diameter×20 cm length) using hexane and t-butyl methyl ether (10:1) afforded 1.1 g (42%) of (5S)-N-((2S)-2-benzoylpropanoyl)-5-ethenylpyrrolidin-2-one (24a) as a thick oil: $^1$H NMR (CDCl$_3$) δ1.44-1.46 (d, J=6.5 Hz, 3 H), 1.64-1.80 (m, 1 H), 2.12-2.20 (m, 1 H), 2.42-2.84 (m, 2 H), 4.12-4.21 (q, J=6.4 Hz, 1 H), 4.38-4.47 (m, 1 H), 4.58-4.67 (m, 1 H), 4.89-4.91 (m, 1 H), 5.06-5.19 (m, 2 H), 5.77-5.85 (m, 1 H), 7.28-7.40 (m, 5 H); $^{13}$C NMR (CDCl$_3$) δ174.8, 173.5, 137.7, 135.3, 128.0, 127.7, 127.4, 115.1, 74.6, 71.6, 31.3, 24.0, 18.1; IR (neat) 3066 (w), 3033 (w), 2939 (w), 1740 (vs), 1708 (vs), 1455 (s), 1370 (s), 1277 (s), 1148 (s), 1113 (s), 739 (s) cm$^{-1}$.

STEP E HYDROLYSIS

(5S)-5-Ethenylpyrrolidin-2-one (6) from (5S)-N-((2S)-2-benzoylpropanoyl)-5-ethenylpyrrolidin-2-one (24a)

To a solution of 1.0 g (3.5 mmol) of (5S)-N-((2S)-2-benzoylpropanoyl)-5-ethenylpyrrolidin-2-one (24a) in methanol (20 mL) and water (5 mL) is added 240 mg (1.7 mmol) of potassium carbonate. The resulting reaction mixture is stirred at 25° C. for 1 hour. An additional 20 mL of water is added and the solution is extracted with methylene chloride (3×25 mL). The combined organic extracts are dried over magnesium sulfate. Concentration and purification by flash chromatography on silica gel using hexane and ethyl acetate (9:1) affords (5S)-5-ethenylpyrrolidin-2-one (6).

EXAMPLE 6

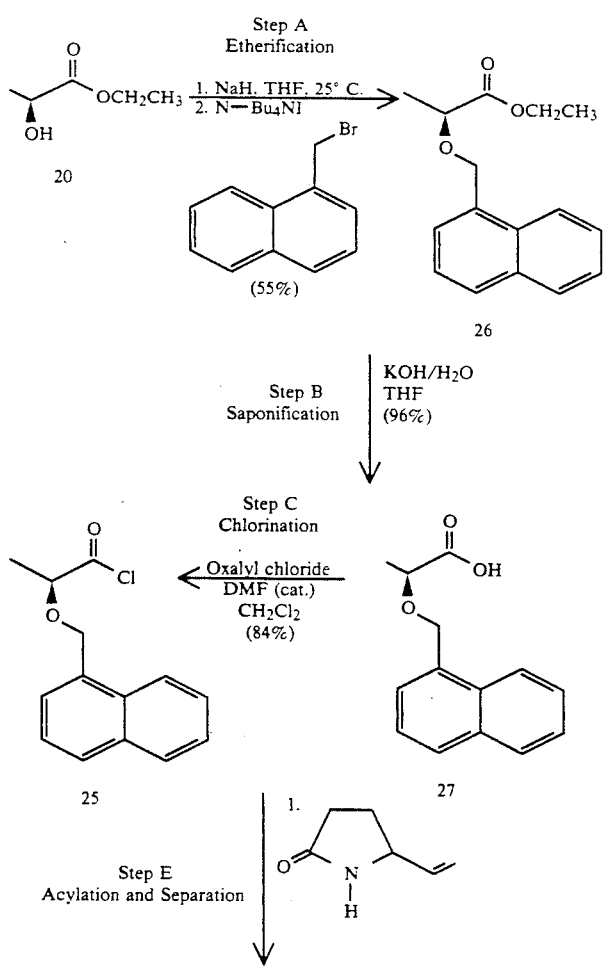

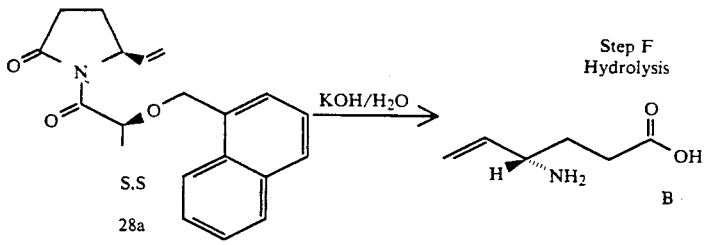

Step F
Hydrolysis

STEP A ETHERIFICATION

Ethyl (2S)-2-(u-(1-Methylnaphthlenyloxy)propanate (26)

To a slurry of 3.7 g (110 mmol) of sodium hydride (60% in mineral oil) in tetrahydrofuran (100 mL) at 25° C. was added a solution of 12.0 g (102 mmol) of (S)-ethyl lactate (20) in tetrahydrofuran (50 mL) dropwise over a 30 min period under a nitrogen atmosphere. The resulting solution was then allowed to stir at 25° C. for an additional 1 h to ensure complete anion formation. To the anion was added 40.6 g (110 mmol) of tetra-n-butylammoniun iodide. A solution of 25.0 g (113 mmol) of 1-(α-bromomethyl)naphthalene in tetrahydrofuran (100 mL) was added dropwise to the reaction mixture over a 5 min period. The reaction was complete within 72 h (over the weekend) at 25° C., during which time a solid precipitate formed. The reaction mixture was filtered through a coarse sintered glass funnel containing Celite ®. The solid was washed with diethyl ether (50 mL). The filtrate was washed with a saturated aqueous sodium chloride solution (2×300 mL) and dried (MgSO4). Concentration and purification by flash chromatography on silica gel (EM silica gel 60, 0.040–0.063 partical size, 230–400 Mesh, column size: 7 cm diameter×20 cm length) using hexane and ethyl acetate (9:1) afforded 14.5 g (55%) of ethyl (2S)-2-(α-(1-methylnaphthlenyloxy)propanate (26) as an oil: $^1$H NMR (CDCl$_3$) δ1.31–1.36 (t, J=7.2 Hz, 3 H), 1.48–1.51 (d, J=6.7 Hz, 3 H), 4.13–4.20 (q, J=6.7 Hz, 1 H), 4.24–4.31 (q, J=7.1 Hz, 2 H), 4.85–4.88 (d, J=11.5 Hz, 1 H), 5.25–5.29 (d, J=11.5 Hz, 1 H), 7.39–7.62 (m, 4 H), 7.83–7.90 (m, 2 H), 8.32–8.35 (d, J=8.3 Hz, 1 H); $^{13}$C NMR (CDCl$_3$) δ173.1, 133.8, 133.1, 131.9, 128.8, 128.4, 126.7, 126.2, 125.7, 125.1, 124.3, 74.1, 70.5, 60.7, 18.7, 14.1; IR (neat) 3051 (w), 2985 (w), 2940 (w), 1744 (vs), 1200 (s), 1144 (vs), 1021 (s), 777.6 (vs) cm$^{-1}$.

STEP B DEPROTECTION (2S)-2-(α-(1-Methylnaphthlenyloxy)propanonic Acid (27)

To a solution of 4.2 g (74 mmol) of potassium hydroxide in water (150 mL) and tetrahydrofuran (150 mL) was added 13.5 g (52 mmol) of ethyl (2S)-2-(α-(1-methylnaphthlenyloxy)propanate (26). The reaction mixture was allowed to stir overnight at room temperature. The reaction solution was acidified to pH 2 with concentrated hydrochloric acid and and extracted with diethyl ether (3×200 mL). The combined extracts were washed with an aqueous saturated sodium chloride solution (1×300 mL) and dried (MgSO4). Filtration and concentration afforded 11.6 g (96%) of crude (2S)-2-(α-(1-methylnapthlenyloxy)propanonic acid (27) as an orange oil: 1 H NMR (CDCl$_3$) δ1.45–1.48 (d, J=6.9 Hz, 3 H), 4.11–4.18 (q, J=6.9 Hz, 1 H), 4.84–4.88 (d, J=11.6 Hz, 1 H), 5.21–5.25 (d, J=11.6 Hz, 1 H), 7.38–7.55 (m, 4 H), 7.79–7.85 (m, 2 H), 8.19–8.21 (d, J=8.2 Hz, 1 H); $^{13}$C NMR (CDCl$_3$) δ176.9, 133.8, 132.7, 131.8, 128.9, 128.4, 126.9, 126.3, 125.8, 125.1, 124.0, 73.6, 70.5, 67.8, 25.4, 18.4; IR (neat) 3660–2600 (br), 3051 (s), 2987 (s), 1723 (vs), 1235 (s), 1169 (s), 1115 (vs), 801 (s), 778 (s) cm$^{-1}$.

STEP C CHLORINATION (2S)-2-(α-(1-Methylnaphthlenyloxy)propanoyl Chloride (25)

To a mixture of 10.0 g (43 mmol) of (2S)-2-(α-(1-methylnapthlenyloxy)propanonic acid (27) and 5 drops of N,N-dimethylformamide in methylene chloride (150 mL) at 0° C. under a nitrogen atmosphere was added 32.6 mL (65 mmol) of a 2M solution of oxalyl chloride in methylene chloride dropwise over a 1 h period. The reaction mixture was allowed to stir at room temperature overnight. The solvent and any excess oxalyl chloride was removed by rotary evaporation and dried (under vacuum) to afford 9.1 g (84%) of (2S)-2-(α-(1-methylnaphthlenyloxy)propanoyl chloride (25) as a crude yellow liquid: $^1$H NMR (CDCl$_3$) δ1.58–1.60 (d, J=6.8 Hz, 3 H), 4.38–4.44 (q, J=6.8 Hz, 1 H), 4.87–4.91 (d, J=11.6 Hz, 1 H), 5.31–5.35 (d, J=11.6 Hz, 1 H), 7.48–7.67 (m, 4 H), 7.91–7.96 (m, 2 H), 8.23–8.26 (d, J=8.2 Hz, 1 H); $^{13}$C NMR (CDCl$_3$) δ175.8, 133.8, 132.0, 131.7, 129.3, 128.6, 127.2, 126.5, 126.0, 125.2, 123.9, 81.4, 70.9, 18.2; IR (neat) 3051 (w), 2941 (w), 1831 (vs), 1779 (vs), 1513 (s), 1445 (w), 1169 (s), 1109 (s), 910 (s), 893 (s), 801 (vs), 778 (vs) cm$^{-1}$.

STEP D ACYLATION AND SEPARATION

N-Acylation of 5-Vinylpyrrolidin-2-one with (2S)-2-(α-(1-Methylnaphthlenyloxy)propanoyl Chloride (25)

To a solution of 60% sodium hydide (336 mg, 10.0 mmol) and toluene (20 mL) at 0° C. was added dropwise a solution of 5-vinylpyrrolidin-2-one (1.0 mg, 9.0 mmol) in toluene (10 mL) over a 10 min period. The cooling bath was removed and the solution was allowed to warm to 25° C. to ensure complete generation of the anion. To the anion at 25° C. was added dropwise a solution of (2S)-2-(α-(1-methylnaphthlenyloxy)propanoyl chloride (25, 2.5 g, 10.0 mmol) in toluene (10 mL) over a 10 min period. TLC indicated that the reaction was complete upon addition of the acid chloride (silica gel plates; hexane and t-butyl methyl ether, 1:1). Water (50 mL) was added to the reaction mixture and the phases were separated. The aqueous phase was extracted with diethyl ether (2×40 mL). The combined organic phases were washed with a saturated aqeous sodium bicarbonate solution (1×100 mL) and dried (MgSO4). Concentration and purification by flash chromatography on silica gel (EM silica gel 60, 0.040–0.063 partical size, 230-400 Mesh, column size: 6.5 cm diameter×20 cm length) using hexane and t-buthyl methyl ether (10:1) afforded 1.1 g (38%) of (5S)-N-((2S)-2-(α-(1-methylnaphthlenyloxy)propanoyl)-5-ethenylpyrrolidin-2-one (28a) as a thick oil: $^1$H NMR (CDCl$_3$) δ1.49-1.51 (d, J=6.6 Hz, 3 H), 1.89-1.96 (m, 1 H), 2.19-2.30 (m, 1 H), 2.51-2.54 (m, 1 H), 2.61-2.68 (m, 1 H), 4.88-4.84 (d, J=10.3 Hz, 1 H), 4.93-4.97 (t, J=6.4 Hz, 1 H), 5.12-5.30 (m, 4 H), 5.80-5.87 (m, 1 H), 7.41-7.60 (m, 4 H), 7.82-7.88 (m, 2 H), 8.29-8.31 (d, J=8.3 Hz, 1 H); $^{13}$C NMR (CDCl$_3$) δ174.9, 173.6, 135.4, 133.6, 133.4, 131.8, 128.6, 128.6, 126.7, 126.1, 125.6, 125.0, 124.3, 115.3, 74.8, 70.2, 57.7, 31.5, 42.1, 18.3; IR (neat) 3051 (w), 2985 (w), 1737 (vs), 1702 (vs), 1457 (w), 1229 (s), 1108 (s), 803 (s), 780 (s) cm$^{-1}$.

STEP E HYDROLYSIS (4S)-4-Amino-5-hexenoic Acid (B) from (5S)-N-((2S)-2-(α-(1-Methylnaphthlenyloxy)-propanoyl)-5-ethenylpyrrolidin-2-one (28a)

A solution of diastereomer 28a (1.0 g, 3.1 mmol) and 87% potassium hydroxide (392 mg, 7.0 mmol) in water (2 mL) is refluxed for 2 hours. The solution is allowed to cool to room temperature. Additional water is added (15 mL) and the solution is acidified to pH 7 with concentrated hydrochloric acid. Extraction with diethyl ether (3×15 mL) removes the cleaved chiral auxiliary. The aqueous phase is acidified to pH 5.5 with concentrated hydrochloric acid and extracted with diethyl ether (3×15 mL). The second series of organic extracts is combined and dried (MgSO$_4$). Concentration by rotary evaporation affords (4S)-4-amino-5-hexenoic acid (B).

EXAMPLE 7

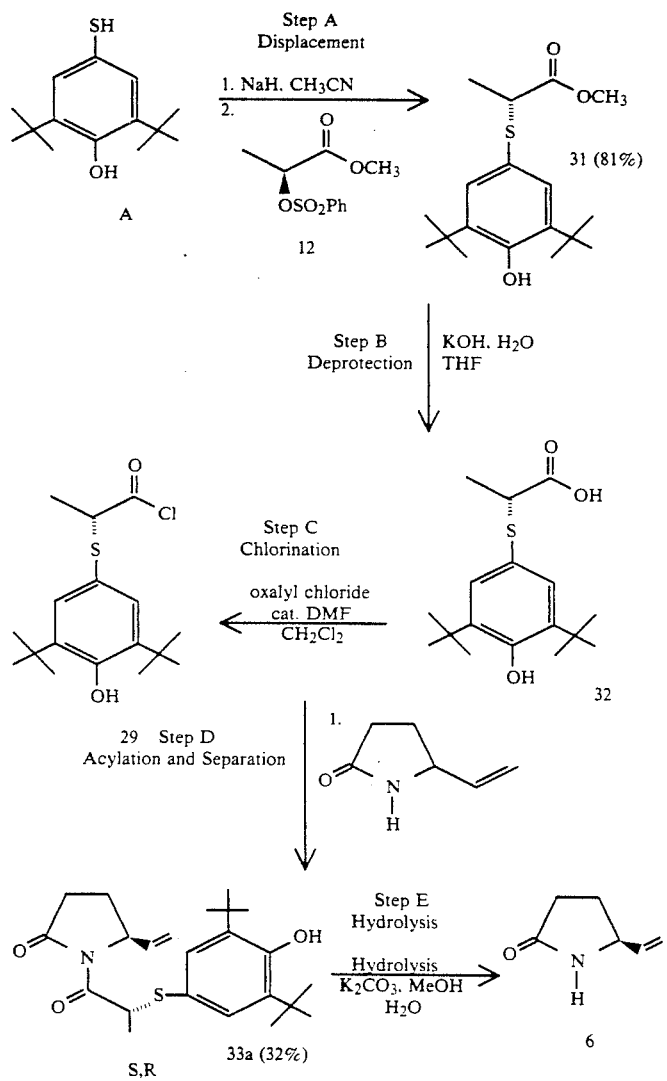

STEP A DISPLACEMENT

Methyl (2R)-2-(3,5-Di-t-butyl-4-hydroxyphenyl)thiopropanoate (31)

To a solution of 60% sodium hydride in mineral oil (7.0 g, 0.20 mol) and acetonitrile (200 mL) under a nitrogen atmosphere was added dropwise a solution of 2,6-di-t-butyl-4-mercaptophenol (A) (53.7 g, 0.23 mol, 90%) in acetonitrile (100 mL) over a 1 h period. The reaction mixture was stirred at 25° C. for an additional hour to ensure complete anion generation. To the mercaptophenol anion was added a solution of methyl (2S)-2-(phenylsulfonyloxy)propanate (50 g, 0.20 mol, 12) in acetonitrile (100 mL) dropwise over a 1 h period. Upon addition of methyl (2S)-2-(phenylsulfonyloxy)propanate a white precipitate was observed. The reaction mixture was allowed to stir at 25° C. overnight. The mixture was worked-up by filtration through a coarse sintered glass funnel containing was Celite ®. The solvent was removed by rotary evaporation to afford a smelly yellow oil. Purification by flash chromatography on silica gel (EM silica gel 60, 0.040–0.063 partical size, 230–400 Mesh, column size: 10 cm diameter×30 cm length) using hexane and ethyl acetate (9:1) afforded 51.3 g (81%) of methyl (2R)-2-(3,5-di-t-butyl-4-hydroxyphenyl)thiopropanoate (31) as a thick oil: $^1$H NMR (CDCl$_3$) δ1.42–1.45 (m, 21 H), 3.60–3.68 (q, J=7.2 Hz, 1 H), 3.67 (s, 3 H), 5.33 (s, —OH, 1 H), 7.29 (s, 2 H); $^{13}$C NMR (CDCl$_3$) δ173.3, 154.6, 136.6, 131.8, 122.0, 52.0, 46.0, 34.3, 30.2, 17.4; IR (neat) 3635 (s), 2958 (vs), 2875 (s), 1737 (vs), 1426 (vs), 1237 (vs), 1160 (vs), 855 (w), 774 (w) cm$^{-1}$.

STEP B DEPROTECTION (2R)-2-(3,5-Di-t-butyl-4-hydroxyphenyl)thiopropanoic Acid (32)

To a solution of 4.5 g (80 mmol) of potassium hydroxide in water (200 mL) and tetrahydrofuran (200 mL) was added 21.46 g (70 mmol) of methyl (2R)-2-(3,5-di-t-butyl-4-hydroxyphenyl)thiopropanoate (31). The reaction mixture was allowed to stir overnight at room temperature. The reaction solution was acidified to pH 1.2 with concentrated hydrochloric acid and and extracted with t-butyl methyl ether (3×100 mL). The combined extracts were washed with an aqueous saturated sodium chloride solution (1×300 mL) and dried (MgSO$_4$). Filtration, concentration and recrystallization from hexane and ethyl acetate afforded 18.35 g (90%) of (2R)-2-(3,5-di-t-butyl-4-hydroxyphenyl)thiopropanoic acid (32) as a white crystalline material: m.p. 111°–112° C.; $^1$H NMR (CDCl$_3$) δ1.33–1.46 (m, 21 H), 3.58–3.65 (q, J=7.1 Hz, 1 H), 5.34 (s, —OH, 1 H), 7.33 (s, 2 H), 9.12 (b, —CO$_2$H, 1 H); $^{13}$C NMR (CDCl$_3$) δ178.8, 154.8, 136.7, 131.8, 121.6, 46.0, 34.4, 30.2, 17.1; IR (KBr) 3608 (s), 3570 (s), 2960 (vs), 1692 (vs), 1424 (vs), 1287 (s), 1239 (vs), 1121 (vs), 884 (s), 774 (w) cm$^{-1}$.

STEP C CHLORINATION (2R)-2-(3,5-Di-t-butyl-4-hydroxyphenyl)thiopropanoyl Chloride (29)

To a mixture of 10.0 g (43 mmol) of (2R)-2-(3,5-di-t-butyl-4-hydroxyphenyl)thiopropanoic acid (32) and 7 drops of N,N-dimethylformamide in methylene chloride (150 mL) at 0° C. under a nitrogen atmosphere was added 34.0 mL (68 mmol) of a 2M solution of oxalyl chloride in methylene chloride dropwise over a 1 h period. The reaction mixture was allowed to stir at room temperature overnight. The solvent and any excess oxalyl chloride was removed by rotary evaporation and dried (under vacuum) to afford 11.15 g (99.8%) of (2R)-2-(3,5-di-t-butyl-4-hydroxyphenyl)thiopropanoyl chloride (29) as a thick yellow liquid: $^1$H NMR (CDCl$_3$) δ1.43 (s, 18 H), 147–1.49 (d, J=7.0 Hz, 3 H), 3.83–3.90 (q, J=7.0 Hz, 1 H), 5.29 (s, —OH, 1 H), 7.32 (s, 2 H); IR (neat) 3631 (vs), 2962 (vs), 2875 (s), 1773 (vs), 1426 (vs), 1239 (s), 1156 (s), 1123 (s), 918 (vs), 888 (w), 774 (w) cm$^{-1}$.

STEP D ACYLATION AND SEPARATION

N-Acylation of 5-Vinylpyrrolidin-2-one with (2R)-2-(3,5-Di-t-butyl-4-hydroxyphenyl)thiopropanyl chloride (29)

To a solution of 60% sodium hydride (665 mg, 19.0 mmol) and toluene (40 mL) at 0° C. was added dropwise a solution of 5-vinylpyrrolidin-2-one (2.0 g, 18.0 mmol) in toluene (20 mL) over a 30 min period. The cooling bath was removed and the solution was allowed to warm to room temperature and stir there for a 30 min period to ensure complete anion generation. To the anion at 25° C. was added dropwise a solution of (2R)-2-(3,5-di-t-butyl-4-hydroxyphenyl)thiopropanoyl chloride (29, 6.21 g, 19.0 mmol) in toluene (20 mL) over a 20 min period. TLC indicated that the reaction was complete upon addition of the acid chloride (silica gel plates; hexane and ethyl acetate, 2:1). Water (100 mL) was added to the reaction and the phases were separated. The aqueous phase was extracted with t-butyl methyl ether (2×100 mL). The combined organic phases were washed with a saturated aqueous sodium bicarbonate solution (1×250 mL) and dried (MgSO$_4$). Concentration and purification by flash chromatography on silica gel (EM 60, 0.040–0.063 partical size, 230–400 Mesh, column size: 4.5 cm diameter×24 cm length) using hexane and ethyl acetate (10:1) afforded 2.32 g (32%) of (5S)-N-((2R)-2-(3,5-di-t-butyl-4-hydroxyphenyl)thiopropanoyl)-5-ethenylpyrrolidin-2-one (33a) as a white crystalline material: mp 105°–106° C.; $^1$H NMR (CDCl$_3$) δ1.37–1.42 (m, 21 H), 1.79–1.86 (m, 1 H), 1.97–2.05 (m, 1 H), 2.32–2.41 (m, 1 H), 2.57–2.67 (m, 1 H), 4.71–4.75 (t, J=6.8 Hz, 1 H), 5.03–5.17 (m, 3 H), 5.33 (s, —OH, 1 H), 5.78–5.87 (m, 1 H), 7.23 (s, 2 H); 13C NMR (CDCl$_3$) δ174.7, 172.6, 154.7, 136.3, 135.7, 132.7, 120.9, 115.3, 58.8, 44.1, 34.3, 31.9, 30.2, 23.9, 16.4; IR (KBr) 3581 (s), 2964 (s), 1748 (vs), 1684 (vs), 1426 (s), 1345 (s), 1227 (vs), 1198 (s), 917 (w), 885 (w) cm$^{-1}$.

STEP E HYDROLYSIS (5S)-5-Ethenylpyrrolidin-2-one (6) from (5S)-N-((2R)-2-(3,5-Di-t-butyl-4-hydroxyphenyl)thiopropanyl)-5-ethenylpyrrolidin-2-one (33a)

To a solution of 1.5 g (3.7 mmol) of (5S)-N-((2R)-2-(3,5-di-t-butyl-4-hydroxyphenyl)thiopropanyl)-5-ethenylpyrrolidin-2-one (33a) in methanol (25 mL) and water (5 mL) is added 257 mg (1.9 mmol) of potassium carbonate. The reaction mixture is allowed to stir at room temperature for 1.5 hours. Additional water (20 mL) is added and the solution is extracted with methylene chloride (3×40 mL). The combined organic extracts should be dried over magnesium sulfate. Concentration and purification by flash chromatography on silica gel (EM 60, 230–400 mesh) using hexane and ethyl acetate (9:1) affords (5S)-5-ethenylpyrrolidin-2-one (6).

EXAMPLE 8

Step A
Displacement

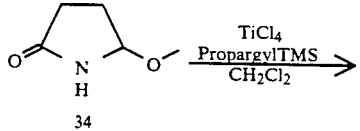

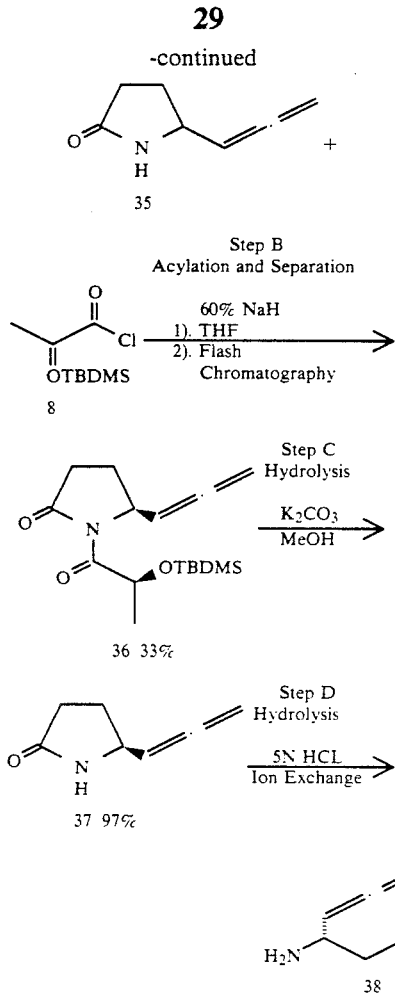

STEP A DISPLACEMENT 5-(1,2-Propadienyl)pyrrolidin-2-one (35)

A solution of 5-methoxypyrrolidin-2-one (34) (2.55 g, 33.3 mmol), propargyl trimethylsilane (3.77 g, 33.7 mmol) and $CH_2Cl_2$ (100 mL) was cooled to 0° C. To this solution was added $TiCl_4$ (4.9 mL, 44.4 mmol) in $CH_2Cl_2$ (20 mL) over a 15 min period at $\leq 3°$ C. After stirring for 30 min, the reaction was poured through silica gel (30 g), rinsed with $CH_2Cl_2$ (100 mL), and this initial filtrate (120 mL) discarded. The silica gel was then washed with 5% $MeOH/CH_2Cl_2$ (100 mL) followed by 10% $MeOH/CH_2Cl_2$ (100 mL), and the combined filtrates were washed with water (50 mL). The aqueous layer was back extracted with $CH_2Cl_2$ (4×30 mL), and the combined organic layers dried over $MgSO_4$ and rotary evaporated ($\leq 30°$ C.) to give 5-(1,2-propadienyl)-2-pyrrolidinone (35) as a brown oil: TLC (Eluant A) $R_f=0.45$; $^1H$ NMR: δ6.6 (br s, 1 H, NH); 5.17 (ddd, $^3J_{64}\approx{}^4J_{68}\approx{}^4J_{68}\approx 6.6$ Hz, 1 H, H6); 4.88 (d, $^4J_{68'}=6.4$, 1 H, H8'); 4.21 (m, 1 H, H5); 2.35 (m, 3 H, H3, H4, H4'); 1.93 (m, 1 H, H3'); Cl Mass spec: m/z 124 (MH+), 84 (MH+—$C_3H_4$).

STEP B ACYLATION AND SEPARATION (5S)-N-((2S)-2-(1,1-Dimethylethyl)dimethylsilyloxy)-propanoyl)-5-(1,2-propadiethyl)pyrrolidin-2-one (36)

To a solution of NaH (80%, 1.60 g, 55.5 mmol) in THF (60 mL) at 0° C. was added 5-(1,2-propandienyl)-pyrrolidin-2-one (35) (2.73 g, 22.2 mmol) in THF (20 mL) over a 10 minute period. The mixture was allowed to warm to room temperature, and a solution of (2S)-2-((1,1-dimethylethyl)dimethylsilyloxy)propanoyl chloride (18) (7.4 g, 33.3 mmol) in THF (20 mL) was added over a 10 minute period. After stirring for 2 h at room temperature, the solvent was removed by rotary evaporation ($\leq 30°$ C.) to afford a brown oil. This oil was dissolved in $CH_2Cl_2$ (100 mL), washed with $H_2O$ (30 mL) and saturated $NaHCO_3$ (30 mL) and dried over $MgSO_4$. Rotary evaporation (30° C.) and purification by flash chromatography (15% EtOAc/Hexane, 200 mL silica gel) gave (5S)-N-((2S)-2-(1,1-dimethylethyl)-dimethylsilyloxy)propanoyl)-5-(1,2-propadiethyl)pyrrolidin-2-one (2.23 g, 33%) as a clear oil: TLC (eluant B) $R_f=0.35$; $^1H$ NMR: δ5.36 (q, $^3J_{H-Me}=6.5$ Hz 1 H, —C(O)CHMEOTBDMS); 5.30 (ddd, $^3J_{65}=4.3, ^4J_{68}=6.4, ^4J_{68'}=6.5$, 1 H, H6); 4.91 (m, 1 H, H5); 4.86 (dd, $^4J_{86}=6.4, ^5J_{85}=0.8$, 1 H, H8); 4.85, $^4J_{8'6}=6.5, ^5J_{8'5}=1.2$, 1 H H8'); 2.67 (ddd, $^2J_{33'}=17.6, ^3J_{34}=11.4, ^3J_{34'}=9.0$, 1 H, H3); 2.45 (ddd, $^3J_{3'4}=8.7, ^3J_{3'4}=2.4$, 1 H, H3'); 2.21 (dddd, $^2J_{44'}\approx12.5, ^3J_{43}=11.4, ^3J_{43'}=8.7, ^3J_{45}\approx8.5$, 1 H, H4); 2.03 (dddd, $^3J_{4'3}=9.0, ^3J_{43'}=2.4, ^3J_{4'5}\approx2.2$, 1 H, H4'), 1.34 (d,$^3J_{H-Me}=6.6$, 3 H, —C(O)CHMeOTBDMS); 0.87 (s, 9 H, —OSiMe$_2$t-butyl); 0.06 and 0.02 (s, 3 H ea, —OSiMe$_2$t-butyl).

STEP C HYDROLYSIS (5S)-5-(1,2-Propadienyl)pyrrolidin-2-one (37)

A solution of (5S)-N-((2S)-2-(1,1-dimethylethyl)-dimethylsilyloxy)propanoyl)-5-(1,2-propadienyl)pyrrolidin-2-one (2.70 g, 8.7 mmol), $K_2CO_3$ (0.6 g, 4.4 mmol), and MeOH (40 mL) was stirred at room temperature for 1.5 hours. The solvent was removed by rotary evaporation ($\leq 30°$ C.) to give a yellow gum. This gum was dissolved in $CH_2Cl_2$ (20 mL), filtered to remove salts and applied to a silica gel plug (50 g). This plug was rinsed with 10% $MeOH/CH_2Cl_2$, discarding the initial eluent which contains the chiral auxiliary, to give (5S)-5-(1,2-Propadienyl)pyrrolidin-2-one (1.04 g, 97%) as a clear oil: TLC (Eluent A) $R_f=0.45$; $^1H$ NMR: δ6.6 (br s, 1 H, NH); 5.17 (ddd, $^3J_{64}\approx{}^4J_{68}\approx{}^4J_{68}\approx 6.6$ Hz, 1 H, H6); 4.88 (d, $^4J_{68}\approx6.7$ Hz, 1 H, H8); 4.88 (d, $^4J_{68'}=6.4$, 1 H, H8'); 4.21 (m, 1 H, H5); 2.35 (m, 3 H, H3, H4, H4'); 1.93 (m, 1 H, H3'); Cl Mass spec: m/z 124 (MH+), 84 (MH+—$C_3H_4$).

STEP D HYDROLYSIS (4S)-4-Amino-5,6-heptadienoic acid (38)

A solution of (5S)-5-(1,2-propadienyl)pyrrolidin-2-one (37) (1.1 g, 9.0 mmol), 5N HCl (10 mL) and $H_2O$ (4 mL) was heated to 80° C. for 18 hours. the solution was cooled, concentrated and neutralized to pH 6 with 1N NaOH. This solution was put on a Dowex 1×2-100 ion exchange column (OH) form. The column was rinsed with distilled $H_2O$ (800 mL) and the compound was removed with 0.5N acetic acid. Lyophilization gave (4S)-4-amino-5,6-heptadienoic acid as an off-white foamy solid (1.01 g, 80%).

What is claimed is:

1. An optical isomer of the formula:

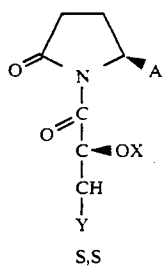

S,S in which A is represented by —CH=CH$_2$ or —CH=C=CH$_2$, and X and Y are each simultaneously represented by

| Y | X |
|---|---|
| H | —Si(CH$_3$)$_2$C(CH$_3$)$_3$ |
| phenyl | —Si(CH$_3$)$_2$C(CH$_3$)$_3$ |
| H | —CH$_2$-phenyl |
| H | —CH$_2$-naphthyl |

2. An optical isomer of the formula:

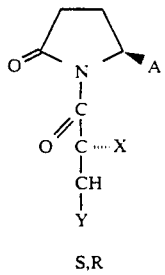

S,R in which A is represented by —CH=CH$_2$ or —CH=C=CH$_2$, and X and Y are each simultaneously represented by

| Y | X |
|---|---|
| H | —O-phenyl-di-tert-butyl |

-continued

| Y | X |
|---|---|
| H | 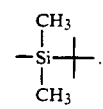 |
| H | 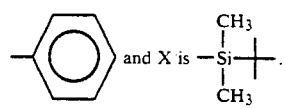 |

3. A compound according to claim 1 in which Y is H and X is

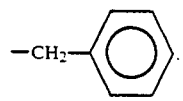

4. A compound according to claim 1 in which Y is phenyl and X is —Si(CH$_3$)$_2$C(CH$_3$)$_3$.

5. A compound according to claim 1 in which Y is H and X is

—CH$_2$-phenyl.

6. A compound according to claim 1 in which Y is H and X is

—CH$_2$-naphthyl.

7. A compound according to claim 2 in which Y is H and X is

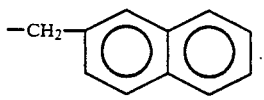

8. A compound according to claim 2 in which Y is H and X is

9. A compound according to claim 1 in which Y is H and X is
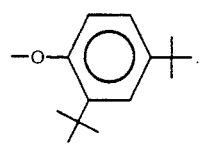
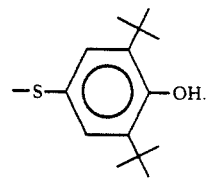
* * * * *

UNITED STATES PATENT AND TRADEMARK OFFICE
CERTIFICATE OF CORRECTION

PATENT NO. : 5,208,345
DATED : May 4, 1993
INVENTOR(S) : Johnathan C. Evans

It is certified that error appears in the above-identified patent and that said Letters Patent is hereby corrected as shown below:

Column 1, Line 47 patent reads: "trifluoroacteic" and should read -- trifluoroacetic -- .
Column 1, Line 49 patent reads: " application Serial No. 432,707 " and should read --   Application 432,707   --.
Column 3, Line 44 patent reads: " minuites " and should read -- minutes   --.
Column 13, Line 46 patent reads: "6 1.29 " and should read --   δ 1.29 --.
Column 17, Line 10 patent reads: "675 m9" and should read -- 675 mg --.
Column 23, Line 14 patent reads: " -2-(u-(1 " and should read --   -2-(a-(1   --.
Column 23, Line 66 patent reads: " 1 H" and should read -- $^1$H   --.
Column 27, Line 6 patent reads: " containing was Celite " and should read --   containing Celite   --.
Column 27, Line 42 patent reads: " -CO$_2$ H, 1 H) " and should read -- -CO$_2$H, 1H) --.
Column 28, Line 36 patent reads: " 13C " and should read --   $^{13}$C   --.

Signed and Sealed this

Fourteenth Day of May, 1996

*Attest:*

BRUCE LEHMAN

*Attesting Officer*     Commissioner of Patents and Trademarks